US005673702A

United States Patent [19]
Albrecht et al.

[11] Patent Number: 5,673,702
[45] Date of Patent: Oct. 7, 1997

[54] METHOD AND APPARATUS FOR THE IMPROVED ELECTRONIC DISPLAY OF PHYSIOLOGIC WAVEFORMS

[75] Inventors: Paul Albrecht, Bedford; Jeffrey M. Arnold, Wellesley; Paul E. Grimshaw, Sudbury; Kevin S. Librett, Boston; Richard J. Cohen, Waban, all of Mass.

[73] Assignee: Cambridge Heart, Inc., Bedford, Mass.

[21] Appl. No.: 258,511

[22] Filed: Jun. 10, 1994

[51] Int. Cl.⁶ .................................................. A61B 5/044
[52] U.S. Cl. ........................................................ 128/712
[58] Field of Search ................................. 128/630, 672, 128/688, 695, 696, 699, 710, 712, 731, 733, 774, 782, 900; 364/413.01, 413.02, 413.05, 413.06

[56] References Cited

U.S. PATENT DOCUMENTS

| | | |
|---|---|---|
| 3,752,917 | 8/1973 | Foley et al. . |
| 4,006,737 | 2/1977 | Cherry ................... 364/413.06 |
| 4,295,135 | 10/1981 | Sukonick . |
| 4,934,374 | 6/1990 | Ostlund et al. .......... 728/695 |
| 5,410,473 | 4/1995 | Kangko et al. ........ 364/413.05 |

FOREIGN PATENT DOCUMENTS

0426567A1  8/1991  European Pat. Off. .

OTHER PUBLICATIONS

Cardio Control BV brochure, "Cardio Perfect: PC Based ECG".
Cardio Control BV brochure, "Cardio Perfect: It's lighter and brighter".
Mortara Instrument brochure, "Defining the Horizons of Electrocardiography".
"Caliper for use on a television screen" *Electronic Engineering*, 56 (689) London (May 1984).

*Primary Examiner*—William E. Kamm
*Attorney, Agent, or Firm*—Choate, Hall & Stewart

[57] ABSTRACT

Method and apparatus for improved electronic display and interpretation of physiologic waveforms. The apparatus generates a two-dimensional grid on the video screen simulating the appearance of electrocardiographic recording paper or other physiologic signal recording paper. At least one physiologic signal is superimposed upon the grid for a display of the combined signal and grid. In a preferred embodiment of the invention the grid includes lines some of which are separated by no more than 2.6 millimeters. In another embodiment of the invention the grid includes horizontal or vertical lines of at least two types.

86 Claims, 4 Drawing Sheets

III. WAVEFORM DRAWING

I. SETUP

FIG. 3

II. GRID PAINTING

METHOD AND APPARATUS FOR THE IMPROVED ELECTRONIC DISPLAY OF PHYSIOLOGIC WAVEFORMS

BACKGROUND OF THE INVENTION

Electronic display of physiologic signals on video screens is widely used in the field of patient monitoring. For example, electrocardiographic signals and blood pressure signals are often displayed continuously in time in bedside patient monitors in intensive care units and operating rooms. This means of display is very useful because it allows the physician the ability to continually monitor the patient's physiologic status and immediately detect, for example, changes in the electrical or mechanical function of the patient's cardiovascular system.

Another example of the application of such electronic display of physiologic signals occurs during the conduct of exercise stress tests. During such a test a patient has electrodes attached to his body and the patient exercises usually on a treadmill or a bicycle. The level of exercise is increased during the test. The patient is electronically monitored during the exercise and after the exercise in order to detect changes in the pattern of electrical activity in the heart induced by exercise. For example, shifts in the ST segment of the electrocardiogram are used as indicators of insufficient blood flow (ischemia) to regions of the heart muscle. Also, the development of heart rhythm disturbances (arrhythmias) manifested in the monitored electrical signals are used to assess a patient's risk of cardiac dysfunction resulting from arrhythmias. It is important for the patient's safety during an exercise test to have continuous electronic monitoring so that serious ischemia and arrhythmias can be immediately detected and, if needed, the exercise stress stopped and emergency treatment be administered. Unfortunately, the diagnostic changes in the electronically monitored signals are usually too small to be reliably read from a conventional video display on a blank background. For example, ST segment shifts as small as 0.1 millivolts which correspond to 1 millimeter displacements when using a standard gain of one centimeter per millivolt can not be reliably detected on a standard video display nor can subtle variations in other electrocardiographic intervals and amplitudes nor subtle changes in the morphology of electrocardiographic complexes. For this reason during exercise tests the patient's electrocardiogram is intermittently printed out on electrocardiographic paper which includes a grid for aiding diagnosis. Also, if an abnormality is detected the nurse or physician will print out additional recordings on electrocardiographic paper. Because of the need to print out electrocardiograms as rapidly as possible during exercise tests, most exercise stress test monitors are equipped with strip chart recorders rather than laser printers, because the strip chart recorder prints out the electrocardiograms much faster. Thus strip chart recorders are employed as printers even though they are much more expensive than laser printers or other equivalent printers.

The electrocardiographic paper has a fine grid printed on it. Usually horizontal and vertical lines are spaced one millimeter apart. Every fifth horizontal and vertical line is usually emphasized by being thicker and/or darker. The closely spaced (in this case one millimeter) lines may be termed minor grid lines; the emphasized grid lines which are spaced further apart (in this case five millimeters) may be termed major grid lines. The background color of the paper is usually white or light gray in color. The lines are usually either of a red or gray coloring. Electrocardiographic signals are usually displayed with a horizontal speed of 2.5 centimeters per second and a vertical gain of one centimeter per millivolt (occasionally the horizontal speed or vertical gain is altered by an integer multiple). The electrocardiographic signals are usually printed in a black or blue color. This set of characteristics used for printing electrocardiographic signals on paper have been optimized over many years of experience to facilitate the visual interpretation of electrocardiograms. For example, the use of finely gridded electrocardiographic recording paper allows one to visually detect and quantify small changes in a large number of electrocardiographic complexes that can be printed on a standard sheet of 8.5 by 11 inch recording paper. When reading the electrocardiogram printed on the finely gridded electrocardiographic paper, the physician, sometimes with the aid of calipers, can reliably detect and quantify the important, but often subtle, changes in the electrocardiographic signals.

Another example of the electronic monitoring of physiologic signals is the electrocardiographic monitoring of patients during the application of exercise or other physiologic stress used to raise heart rate in order to induce electrical alternans which is an important predictor of an individual's susceptibility to heart rhythm disturbances. (See U.S. patent application Ser. No 08/187,275 "Improved Method and Apparatus for Assessing Myocardial Electrical Stability" by Jeffrey Arnold, Paul Albrecht, Kevin S. Librett and Richard J. Cohen) During such testing it is important to continually monitor the electrocardiograhic signals to detect subtle alterations indicative of ischemia or other adverse effects which might lead the physician to terminate the physiologic stress. Once again the signals needed to be printed on electrocardiographic recording paper to permit detection of such alterations.

Similarly, during the real-time electronic monitoring of physiologic signals in other settings, such as the intensive care unit, emergency room, operating room, or remote monitoring of patients, or the viewing of signals previously recorded electronically from hospitalized or ambulatory patients, the signals displayed on standard video screens can be visually inspected only to detect gross changes. If an abnormality is suspected then the operator will print out short segments of the signals on gridded paper. Visual detection of fine changes and the quantification of such changes generally requires the inspection of the signals on finely gridded paper.

Physiologic signals other than electrocardiographic signals are also most easily interpreted by printing them on gridded paper. Although not as well standardized as electrocardiographic recording paper, paper used for the recording of physiologic signals often has characteristics similar to paper used for electrocardiographic recording with red or gray vertical and horizontal lines spaced one millimeter apart with every fifth line emphasized. A variety of horizontal speeds and vertical gains are used to display the signals which are often printed in blue or black colors. For example, a horizontal speed of 2.5 centimeters per second and a gain of one centimeter per 100 millimeters of mercury is suitable for the recording of arterial blood pressure. Physiologic recording paper has been optimized so that physicians can detect important, but often subtle, features of physiologic waveforms.

The requirement of printing physiologic signals on gridded paper to make accurate diagnoses and measurements is very undesirable. There is a delay in printing the signals so that immediate diagnosis cannot be made. Expensive strip chaff recorders are generally used because they print faster than other kinds of less expensive printers. Generally only short segments of the signals can be displayed on paper so that transient abnormalities may be missed. If a subtle abnormality is not apparent on the video screen, the physician, nurse or other operator will not know to print the signals and the abnormality may be missed altogether. What is needed is a convenient means of visually detecting and quantifying physiologic waveforms without the need to print out all of the signals on gridded paper.

Literature provided by Cardio Control BV, The Netherlands describes the Cardio Perfect personal computer based instrument for recording and displaying the electrocardiogram at rest or during stress testing. The system is capable of displaying a grid on the video screen upon which can be superposed electrocardiographic signals. However, the screen does not simulate the appearance of electrocardiographic or other physiologic recording paper. The screen background color is black rather than white or light gray. The spacing of the grid lines is much greater than the one millimeter spacing which is common in electrocardiographic and other physiologic recording paper. From the printed literature it appears that the space of the lines on the grid is approximately one centimeter. Because of the wide spacing one cannot use the grid to detect and quantify visually subtle alterations in a series of physiologic waveforms. One could enlarge electrocardiographic waveforms from a single beat (or a few beats) and place it on the coarse grid in an attempt to use the grid to measure intervals. However, the resulting display would not simulate electrocardiographic recording on paper where use of a much finer grid allows one to examine a large number of waveforms on a single sheet of paper which is approximately the same size as a standard video screen. A key feature of a video screen display used for real time patient monitoring is the simultaneous display of waveforms corresponding to a large number of heart beats so that the eye can appreciate changes occurring over time. Furthermore, displaying waveforms using the standard gains allows one to display simultaneously waveforms corresponding to multiple heart beats for each of multiple recorded signals. This is particularly important, for example, in electrocardiographic monitoring in which abnormalities of the waveform may appear in only a small fraction of a large number signals recorded from multiple electrodes. Thus attempting to compensate for the presence of only a coarse grid displayed on the screen of the Cardio Perfect system, by greatly enlarging the size of individual waveforms is not satisfactory for patient monitoring.

In addition, the grid displayed in the Cardio Control BV Cardio Perfect system appears to have uniform grid lines rather than major and minor grid lines differing in width and intensity and differing in spacing as is the case for commonly used electrocardiographic and other physiologic recording paper. Also in the display of the Cardio Perfect system the physiologic waveforms are not drawn in such a way to emulate the appearance of a pen drawing on paper. Thus the Cardio Control BV Cardio Perfect system does not present a video display which has the appearance of electrocardiographic recording on paper, nor does it have functionality of the paper recording system which allows one to visually quantify subtle changes occurring in a large number of physiologic waveforms.

Literature provided by Mortara Instrument, Inc. of Milwaukee Wisconsin describes the X-SCRIBE stress testing system. This system similarly is able to display signals on a coarse grid. This system suffers from all the same limitations as the Cardio Perfect system discussed above. The X-SCRIBE system cannot simulate on the video screen display the appearance or functionality of electrocardiograhic pen recording on paper.

SUMMARY OF THE INVENTION

In one aspect, the method according to the invention for displaying at least one physiologic signal on a video screen includes generating a two-dimensional grid on the video screen simulating the appearance of electrocardiographic recording paper or other physiologic signal recording paper. The at least one physiologic signal is superimposed upon the grid for a display of the combined signal and grid. In another aspect of the invention, the grid includes lines some of which are separated by no more than 2.6 millimeters. In yet another aspect of the invention the grid includes horizontal or vertical lines of at least two types.

The format of electrocardiographic or other physiologic recording paper has been optimized to enhance the ability of physicians to visually detect and quantify subtle alterations in physiologic waveform morphology. By displaying such a format on the video screen physicians may not need to print out on paper the physiologic waveforms in order to detect and quantify subtle alterations in physiologic waveforms obtained from patients being electronically monitored. It was not previously appreciated that one could achieve on the video screen the appearance of physiologic waveforms drawn on paper and that doing so would greatly facilitate the ability of physicians and other health professionals to monitor patients. Thus, the present invention greatly improves over the prior art for displaying physiologic signals on a video screen for monitoring patients.

DESCRIPTION OF THE PREFERRED EMBODIMENT

Figure 1:
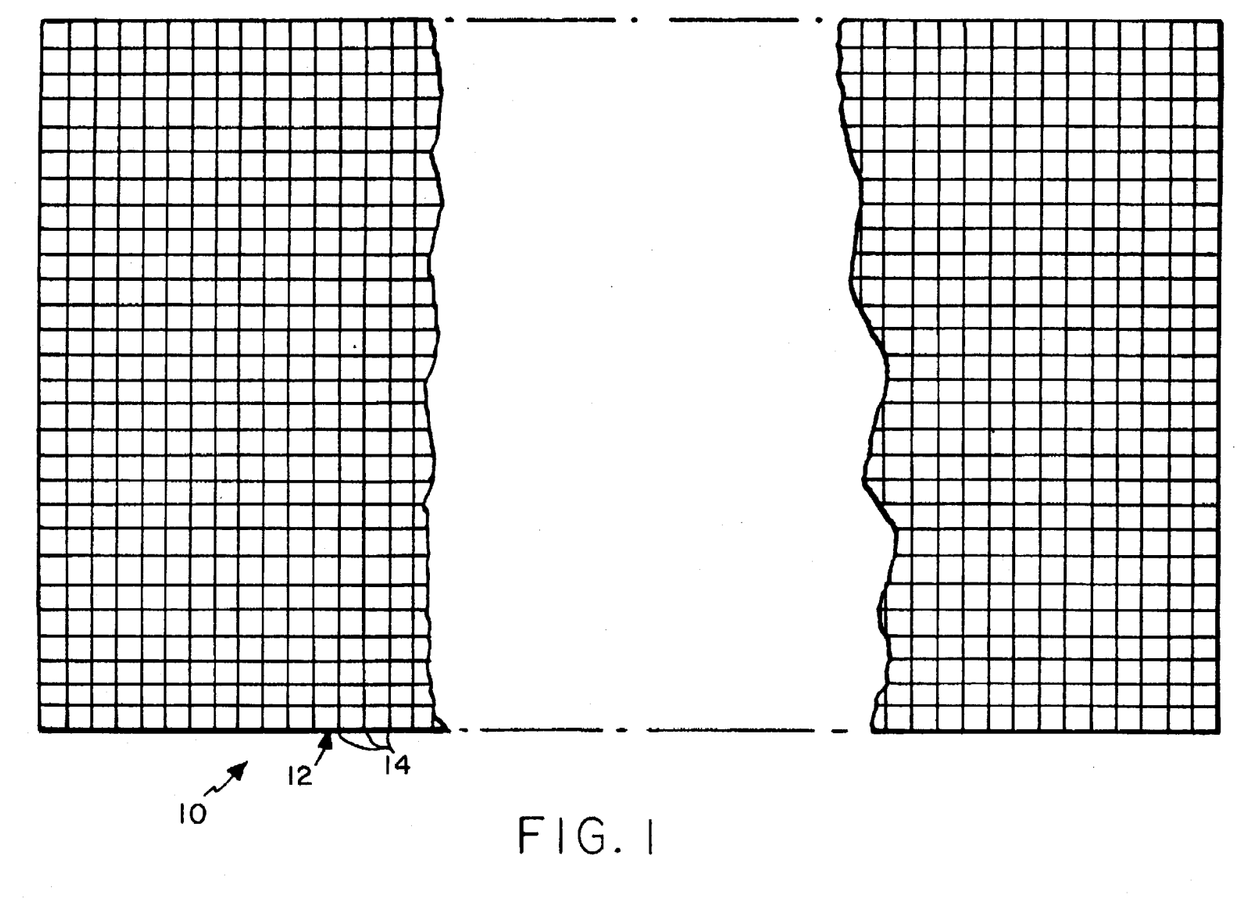
FIG. 1 is a view of electrocardiographic recording paper.
Figure 2:
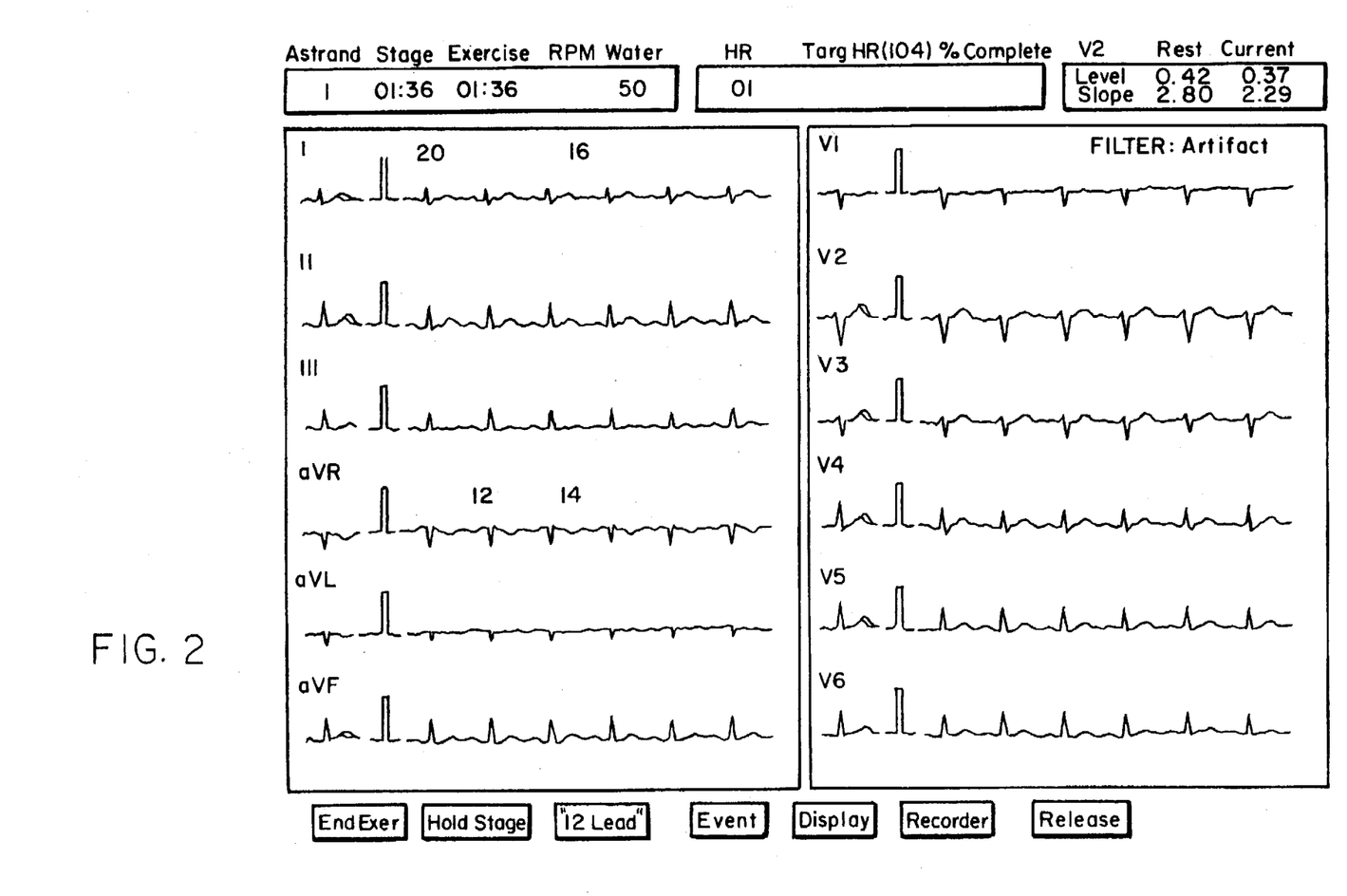
FIG. 2 is a view of a video screen incorporating the gridded pattern and physiological waveforms according to the invention.

A preferred embodiment of this invention involves digitizing the physiologic signals and storing them in a computer. Then one constructs a plot of one or more time epochs of one or more of the signals, superposed on a gridded pattern. Then one displays the plot superposed on the gridded pattern on a video screen. In one preferred embodiment the gridded pattern simulates the appearance of electrocardiographic or other physiologic signal recording paper. With reference to FIG. 1 a standard electrocardiographic grid 10 includes minor lines 12 and major lines 14. In the example of FIG. 1 the minor lines 12 are thinner than the major lines 14 so that they appear less bold. In this standard paper the separation between minor lines 12 is one millimeter while the separation between major lines 14 is five millimeters. In one preferred embodiment the appearance of the displayed plot superposed on the gridded pattern simulates the appearance of pen drawing on a electrocardiographic or other physiologic recording paper. With reference now to FIG. 2 there is shown a display according to the invention. In this figure a series of physiologic signals such as a signal 16 is displayed. Waveform 18 is an average or medium of the waveforms associated with the signal 16. A calibration pulse 20 is also provided. It is preferred that the major and minor lines 12 and 14 be red or gray and the physiologic signal 16 be of a black or blue color. One may also use dithering of the color and/or intensity of the signal to provide smoothing and sub-pixel resolution of the waveforms of the physiologic signals on the video display.

In one preferred embodiment the horizontal or vertical lines when displayed on the video screen are spaced less than 2.6 millimeters apart so as to provide sufficiently fine resolution to facilitate the appreciation of small alterations in physiologic waveform morphology.

The gridded pattern when displayed may have horizontal or vertical lines of two or more types differing, for example, in color, thickness or intensity. In one preferred embodiment there are major grid lines and minor grid lines where the major grid lines are spaced at a larger interval and the minor grid lines are spaced at a smaller interval. Commonly, the major grid lines may appear more intense or thicker than the minor grid lines. In one preferred embodiment, the major grid lines may be spaced at an interval five times the spacing of the minor grid lines. For example, the major grid lines when displayed may be spaced five millimeters apart and the minor grid lines may be spaced one millimeter apart, as is the case in common forms of electrocardiographic and other physiologic signal recording paper.

Figure 3:
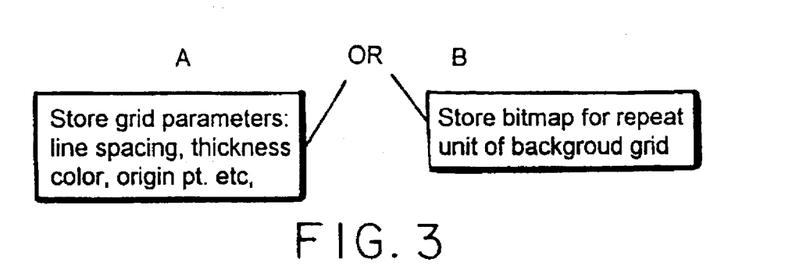
FIG. 3 is a block diagram illustrating set-up of the gridded pattern.

In one preferred embodiment as shown in FIG. 3, the gridded pattern can be generated by electronically storing the grid parameters (such as line spacings, thicknesses, colors and the like) and then drawing the grid lines in the pixels corresponding to a specified region of the video screen using computer line-drawing commands.

Figure 4:
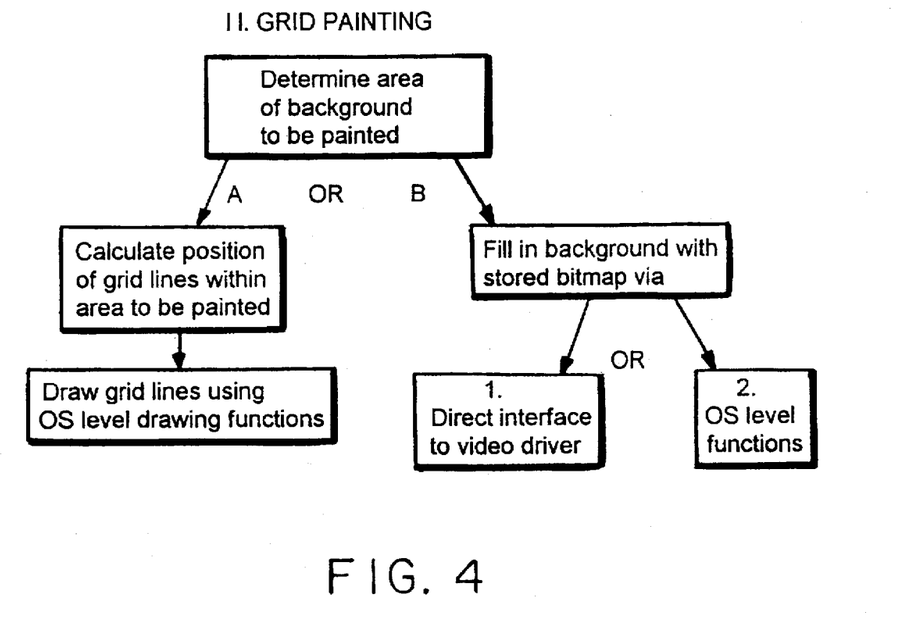
FIG. 4 is a block diagram illustrating grid painting.
Figure 5:
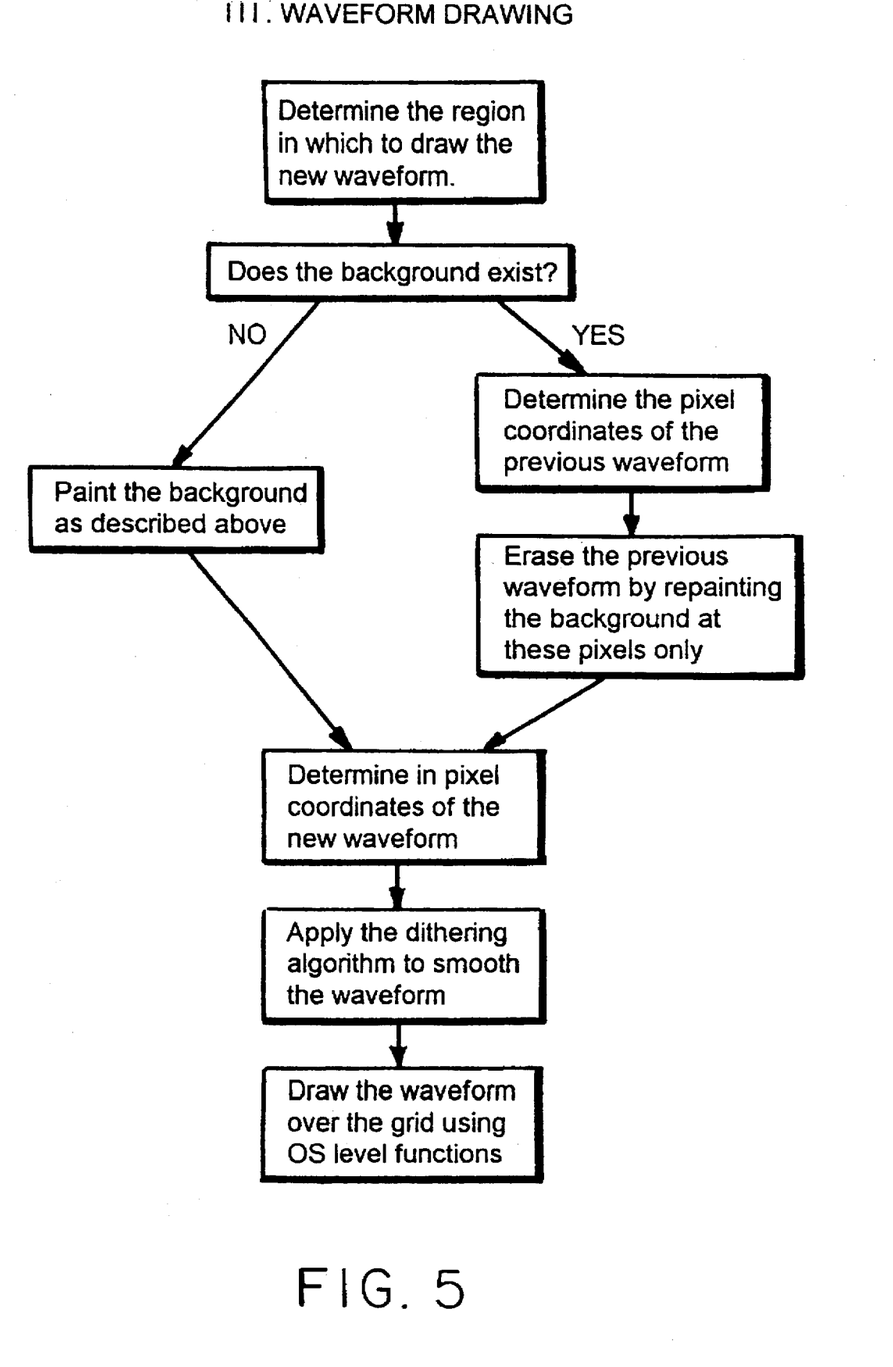
FIG. 5 is a block diagram describing the drawing of waveforms on the grid.

In another preferred embodiment also illustrated in FIG. 3, the gridded pattern is generated by storing a bit-mapped representation of one or more repeating units of the grid and falling in pixels corresponding to a specified region of the video screen with one or more copies of the stored bit-mapped section of the grid. The actual painting of the grid is shown schematically in FIG. 4. The waveform is then superimposed over the grid to provide the look and feel of a pen drawing on grid paper. The physiologic waveform or signal may be drawn incrementally in real time as the ECG (or other data) is being measured, or an entire epoch of data may be drawn in bulk after the measurement is complete. The waveform may be drawn in a color having high contrast with the background grid, and color dithering is used to provide smoothing and sub-pixel resolution of the waveform. Efficient and visually smooth erasing of the waveforms may be accomplished by erasing only those pixels occupied by the waveform. Those pixels alone are redrawn in the colors of the background grid using the above-described techniques. Erasing of waveforms may be performed either in a real-time incremental mode or in a bulk mode where the entire waveform is erased at once. These aspects of waveform drawing are illustrated in FIG. 5.

In one preferred embodiment, the video screen display of the plot of the signals on a gridded pattern may additionally be printed onto paper for long term storage of a hard copy version of the image, or for additional inspection. In another preferred embodiment, the plot of the signals, displayed on the video screen on a gridded pattern, may additionally be printed onto paper on which the gridded pattern has been previously printed in order to reduce the time required for on-line printing.

In another preferred embodiment, distances on the display on the video screen may be measured with the aid of electronic calipers 19 (FIG. 2) which are defined to be one or more cursors which the user may move on the screen (by pushing buttons, levers, or a computer mouse or the like) to demarcate an interval coupled with a screen readout which specifies the length of the interval. Such electronic cursors can be readily implemented using appropriate computer software.

In another preferred embodiment, the displayed plot of the physiologic signals superposed on the gridded pattern is continually updated in time. This is accomplished by fast updating the electronic representation of the plot of the physiologic signals superposed on the gridded pattern at sequential time points and then sequentially displaying the updated electronic representations.

One way known in the art of displaying continually updated signals is the use of an erase bar. An erase bar is an open interval in the plot of a signal which moves just in front of the most recently plotted point and erases the oldest segment of the signal as it advances. An erase bar requires a relatively small mount of computational time since at each time step one only has to plot the newest waveform points and erase the oldest waveform points. In this preferred embodiment the gridded pattern would remain stationary. Another way known in the art of displaying continually updated signs is the use of scrolling. When scrolling the signals the waveforms appear to move across the green. In this embodiment also the gridded pattern may remain stationary or move with the trace.

In another preferred embodiment the displayed plot of the physiologic signals superposed on the gridded array is updated periodically in time for sequential time epochs. In this embodiment the plot superposed on a gridded array corresponding to a preceding time epoch remains fixed until the next time epoch elapses. Then a new plot corresponding to the next time epoch is displayed on the video screen superposed on the gridded array.

In one preferred embodiment the electronic representation of the displayed physiologic signals is updated in time, either continually or periodically, by first redrawing the grid pattern in those pixels occupied by segments of the physiologic waveforms to be eliminated from the display. In redrawing the grid pattern in the appropriate pixels it is understood that the segments of the physiologic waveforms previously drawn in those pixels are erased. Next, the updated portions of the physiologic waveforms are drawn in those pixels which the new segments of the physiologic waveforms will occupy. In drawing the updated portions in the appropriate pixels it is understood that the gridded pattern previously drawn in such pixels is erased thus providing the appearance of the waveform being superposed on the grid.

In another preferred embodiment in which the displayed physiologic signals are updated by scrolling of the waveforms across the screen, the scrolling is accomplished in the following way. The values of the physiologic signals corresponding to the current time epoch are stored in a continually updated circular buffer. This circular buffer contains a finite number of storage elements. The elements contain the values of the signals at sequential time points. The values of the signals at the most recent time point are overwritten onto the storage elements containing the values of the signals at the oldest time points. At each point in time when the plot is updated, the values of the signals stored in the circular buffer are used to create a plot of the values of the signals superposed on a gridded pattern.

In one preferred embodiment the updating of the display of the physiologic signals superposed on a gridded pattern may be halted by the operator to facilitate detailed examination of the waveforms on the screen. In yet another embodiment, the operator may identify one physiologic signal of interest and cause that signal to be expanded on the screen along with comparable expanding of the grid for further analysis.

The method of this invention may be applied to the display of physiologic signals obtained during the measurement of electrical alternans; to the display of physiologic signals obtained during the measurement of cardiac ischemia induced by exercise or other physiologic stress; to the display of physiologic signals obtained in a bedside patient monitor used to monitor a patient in an intensive care unit, operating room, emergency room, other hospital room, ambulance or the like; to the display of physiologic signals obtained during the remote monitoring of a patient; to the display of physiologic signals previously recorded from a patient.

The method of this invention may involve the display of one or more electrocardiographic signals. In particular in one preferred embodiment the method of this invention is applied to the display of 12 or more electrocardiographic signals simultaneously on the video screen. This embodiment is particularly advantageous because it permits the display of all 12 of the electrocardiographic signals conventionally recorded in a standard electrocardiogram. This display may simulate the appearance of a standard 12 signal electrocardiogram printed on electrocardiographic recording paper.

In one preferred embodiment, short segments of multiple signals are displayed, and a longer segment of one or a few signals is displayed. The display of the longer segment of one or a few signals facilitates the identification of heart rhythm disturbance.

In one preferred embodiment the average or median waveform of one or more of the physiologic signals is also displayed on the video screen.

In another preferred embodiment one or more calibration pulses for the physiologic signals are displayed on the video screen (see calibration pulse 20 in FIG. 2).

In one preferred embodiment the horizontal or vertical lines of the grid are omitted and the physiological signals are displayed on a finely ruled vertical or horizontal pattern.

Figure 6:
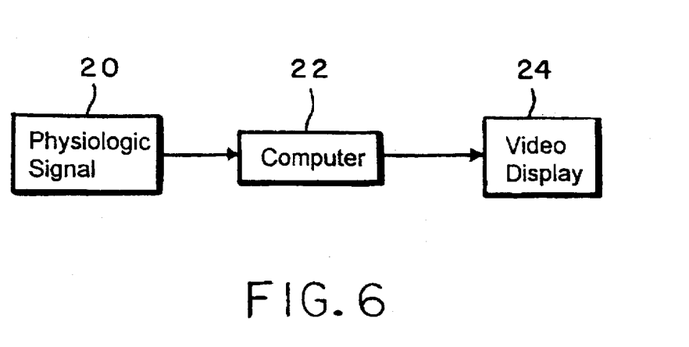
FIG. 6 is a block diagram of the hardware components for carrying out the present invention.

The apparatus for carrying out the present invention is shown in FIG. 6. A physiologic signal block 20 represents the acquisition of physiologic signals either in real time from a patient or previously recorded from a patient. For example, the physiologic block 20 may be standard apparatus for acquiring electrocardiographic signals from a patient. The signals from the block 20 form an input to the computer 22 which is preferably a general purpose digital computer. The computer 22 drives a video display 24 which may be a conventional cathode ray tube display, liquid crystal display or any other suitable video display. A printer 26 may also be connected to the computer 22.

It was not previously appreciated that it would be possible to display physiologic signals on a finely gridded pattern in order to simulate the drawing of physiologic waveforms on gridded electrocardiographic or physiologic recording paper, nor was it realized that doing so would greatly enhance the ability of physicians and other health professionals to visually detect and quantify subtle alterations in physiologic waveform morphology and thus improve their ability to monitor patients. Because the characteristics of electrocardiographic and other physiologic recording paper have been optimized to enable physicians to visually detect and quantify subtle alterations in physiologic waveform morphology, and because physicians and health professionals are so accustomed to the format of physiologic waveforms drawn on gridded recording paper, the method of this invention provides a great improvement over the prior art for displaying physiologic waveforms on a video screen.

What is claimed is:

1. Method for displaying at least one physiologic signal on a video screen comprising:
   acquiring the at least one physiologic signal;
   generating a two-dimensional grid on the video screen, the grid including lines separated by no more than 2.6 millimeters thereby simulating the appearance of physiologic signal recording paper; and
   superimposing the at least one signal on the grid for display of the signal on the grid.

2. The method of claim 1 wherein the physiologic signal recording paper is electrocardiographic recording paper.

3. Method for displaying at least one physiologic signal on a video screen comprising:
   acquiring the at least one physiologic signal;
   generating a two-dimensional grid on the video screen, the grid including major and minor lines; and
   superimposing the at least one signal on the grid for display of the signal on the grid.

4. The method of claims 1 or 3 in which the grid is generated by:
   electronically storing the grid parameters (such as line spacings, thicknesses, colors, and the like); and
   drawing the grid lines in pixels corresponding to a specified region of the video screen using line-drawing commands.

5. The method of claims 1 or 3 in which the grid is generated by:
   storing a bit-mapped representation of at least one repeating units of the grid; and
   filling in pixels corresponding to a specified region of the video screen with at least one copies of the stored bit-mapped section of the grid.

6. The method of claims 1 or 3 in which the grid is of a red color.

7. The method of claims 1 or 3 in which the physiologic signals are superposed on the grid to simulate the appearance of a pen drawing on physiologic recording paper.

8. The method of claim 7 wherein the physiologic recording paper is electrocardiographic paper.

9. The method of claims 1 or 3 in which the physiologic signals are of a black color.

10. The method of claims 1 or 3 in which the superimposing step includes dithering to provide smoothing and sub-pixel resolution of the physiologic signals.

11. The method of claims 1 or 3 comprising an additional step of printing an image of the video screen on paper.

12. The method of claims 1, or 3 comprising an additional step of printing the physiologic signals on paper on which a gridded pattern has been previously printed.

13. The method of claims 1 or 3 comprising an additional step of using electronic calipers to display distances on the video display.

14. The method of claims 1 or 3 in which the superimposing step includes display of the physiologic signals being updated in time.

15. The method of claims 1 or 3 in which the display of the physiologic signals is continually updated in time by:
   updating at sequential points the physiologic signals superposed on the grid; and
   sequentially displaying updated physiological signals.

16. The method of claims 1 or 3 in which the superimposing step includes the display of the physiologic signals continually updated in time by means of use of an erase bar.

17. The method of claims 1 or 3 in which the display of the physiologic signals is continually updated in time by scrolling the physiologic signals over the grid.

18. The method of claim 17 in which the scrolling is accomplished by:

electronically storing a time epoch of the physiologic signals to be displayed in a continually updated circular buffer;

creating a plot of the time epoch of physiologic signals at sequential time points superposed on the grid; and sequentially displaying an updated electronic representation.

19. The method of claims 1 or 3 in which the display of the physiologic signals is periodically updated in time for sequential time epochs by:

first displaying a plot of the physiologic signals superposed on the grid corresponding to a preceding time epoch until a next time epoch elapses; and then displaying a new plot of the signal corresponding to the next time epoch.

20. The method of claims 1 or 2 in which the display of the physiologic signals is updated by:

redrawing the grid pattern in those pixels occupied by the segments of the physiologic waveforms to be eliminated from the display;

drawing the updated portions of the physiologic waveforms in the pixels which the new segments of the physiologic waveforms will occupy.

21. The method of claims 1 or 3 in which the superimposing step includes display of the physiologic signals continually updated, and in which such updating may be halted by an operator.

22. The method of claims 1 or 3 used during the measurement of electrical alternans.

23. The method of claims 1 or 3 used during physiologic stress.

24. The method of claim 23 wherein the physiologic stress is exercise.

25. The method of claims 1 or 3 used in a bedside patient monitor.

26. The method of claims 1 or 3 wherein the generating and superimposing steps are performed on a patient being remotely monitored.

27. The method of claims 1 or 3 wherein the superimposing step uses signals previously recorded from a patient.

28. The method of claims 1 or 3 wherein the acquiring step includes acquiring at least one electrocardiographic signals.

29. The method of claims 1 or 3 where at least 12 electrocardiographic signals are displayed on video screen simultaneously.

30. The method of claims 1 or 3 also comprising a step of displaying an average waveform of at least one of the physiologic signals.

31. The method of claims 1 or 3 also comprising the step of displaying at least one calibration pulses for the physiologic signals.

32. The method of claims 1 or 3 also comprising the step of the operator identifying one physiological signal of interest and causing that signal to be expanded on the screen along with comparable expanding of the grid for further analysis.

33. The method of claims 1 or 3 wherein the superimposing step includes displaying short segments of multiple signals and displaying a long segment of one or a few signals.

34. The method of claims 1 or 3 in which the grid is of a gray color.

35. The method of claims 1 or 3 in which the physiologic signal is of a blue color.

36. The method of claims 1 or 3 in which the display of the physiologic signals is periodically updated, and in which such updating may be halted by an operator.

37. The method of claim 3 in which the lines of the grid appear to be of at least two types differing in color.

38. The method of claim 3 wherein the generating step includes generating vertical and horizontal lines of two types, major and minor, and wherein the major grid lines are spaced at a larger interval and the minor grid lines are spaced at a smaller interval.

39. The method of claim 38 in which the spacing of the major grid lines is five times the spacing of the minor grid lines.

40. The method of claim 38 in which the spacing of the major grid lines is approximately five millimeters and the spacing of the minor grid lines is approximately one millimeter.

41. The method of claim 3 in which the lines of the grid appear to be of at least two types differing in thickness.

42. The method of claim 3 in which the lines of the grid appear to be of at least two types differing in intensity.

43. Apparatus for displaying at least one physiologic signal on a video screen comprising:

a sensor responsive to the at least one physiologic signal;

a computer connected to receive as an input the physiologic signal from the sensor; and a video display screen connected to the computer;

the computer programmed to generate a two-dimensional grid having the appearance of electrocardiograph paper, and further programmed to superimpose the at least one physiologic signal on the grid for display of the signal on the grid.

44. Apparatus for displaying at least one physiologic signal on a video screen comprising:

a sensor responsive to the at least one physiologic signal;

a computer connected to receive as an input the physiological signal from the sensor; and a video display screen connected to the computer;

the computer programmed to generate a two-dimensional grid on the video screen, the grid including lines some of which are separated by no more than 2.6 millimeters, and further programmed to superimpose the at least one physiological signal on the grid for display of the signal on the grid.

45. Apparatus for displaying at least one physiologic signal on a video screen comprising:

a sensor responsive to the at least one physiologic signal;

a computer connected to receive as an input the physiologic signal from the sensor; and a video display screen connected to the computer;

the computer programmed to generate a two-dimensional grid on the video screen, the grid including lines of a least two types, and further programmed to superimpose the at least one physiologic signal on the grid for display of the signal on the grid.

46. The apparatus of claim 43, 44 or 45 in which the grid is generated by programming the computer for electronically storing the grid parameters (such as line spacings, thicknesses, colors, and the like); and drawing the grid lines in pixels corresponding to a specified region of the video screen using line-drawing commands.

47. The apparatus of claim 43, 44 or 45 in which the grid is generated by programming the computer to store a bit-mapped representation of at least one repeating units of the grid; and filling in pixels corresponding to a specified region of the video screen with one or more copies of the stored bit-mapped section of the grid.

48. The apparatus of claims 43, 44 or 45 in which the computer is programmed to provide the grid in a red color.

49. The apparatus of claim 45 in which the computer is programmed so that the lines of the grid appear to be at least two types differing in color.

50. The apparatus of claim 49 wherein the physiologic recording paper is electrocardiographic paper.

51. The apparatus of claims 43, 44 or 45 wherein the computer is programmed so that the physiologic signals are of a black color on the video screen.

52. The apparatus of claims 43, 44 or 45 adapted to provide dithering to produce smoothing and sub-pixel resolution of the physiological signals.

53. The apparatus of claims 43, 44 or 45 further including a printer adapted to printer print an image of the video display on paper.

54. The apparatus of claims 43, 44 or 45 further including a printer and paper including a gridded pattern, the printer adapted for printing the physiologic signals on the previously printed paper.

55. The apparatus of claims 43, 44 or 45 further including electronic calibers adapted to display distances on the video display.

56. The apparatus of claims 43, 44 or 45 adapted to display the physiologic signals updated in time.

57. The apparatus of claims 43, 44 or 45 adapted to display the physiologic signals continually updated in time by updating at sequential time points the physiologic signals superposed on the grid and further adapted for sequentially displaying updated physiological signals.

58. The apparatus of claims 43, 44 or 45 further including an erase bar adapted for continually updating the display of the physiologic signals.

59. The apparatus of claims 43, 44 or 45 adapted to continually update the physiologic signals by scrolling the physiologic waveforms over the grid.

60. The apparatus of claims 43, 44 or 45 in which the computer is programmed for displaying the physiologic signals updated in time for sequential time epochs by first displaying a plot of the physiologic signals superposed on the grid corresponding to a preceding time epoch until a next time epoch elapses and then displaying a new plot of a signal corresponding to a next time epoch.

61. The apparatus of claims 43, 44 or 45 in which the computer is programmed to update the physiologic signals by redrawing the grid pattern on those pixels occupied by the segments of the physiologic waveforms to be eliminated from the display and drawing the updated portions of the physiologic waveform in the pixels which the new segments of the physiologic waveform will occupy.

62. The apparatus of claims 43, 44 or 45 adapted to accomplish scrolling by electronically storing a time epoch of the physiologic signals to be displayed in a continually updated circular buffer and creating a plot of the time epoch of physiologic signals at sequential time points superimposed on the grid and then sequentially displaying an updated electronic representation.

63. The apparatus of claims 43, 44 or 45 wherein the computer is programmed to display the physiologic signals continually updated and in which such updating may be halted by an operator.

64. The apparatus of claims 43, 44 or 45 adapted to respond to electrocardiographic signals display physiologic signals during the measurement of electrical alternans.

65. The apparatus of claims 43, 44 or 45 adapted to display physiologic signals during physiologic stress.

66. The apparatus of claim 65 wherein the physiologic stress is exercise.

67. The apparatus of claims 43, 44 or 45 adapted to display physiologic signals in a bedside patient monitor.

68. The apparatus of claims 43, 44 or 45 adapted to display physiologic signals of a patient being remotely monitored.

69. The apparatus of claims 43, 44 or 45 adapted to display physiologic signals previously recorded from a patient.

70. The apparatus of claims 43, 44 or 45 wherein the physiologic signals displayed include electrocardiographic signals.

71. The apparatus of claims 43, 44 or 45 wherein 12 at least electrocardiographic signals are displayed on the video screen simultaneously.

72. The apparatus of claims 43, 44 or 45 adapted to display an average waveform of at least one of the physiologic signals.

73. The apparatus of claims 43, 44 or 45 adapted to display at least one calibration pulses for the physiologic signals.

74. The apparatus of claims 43, 44 or 45 wherein an operator identifies one physiological signal of interest and the computer is programmed to cause that signal to be expanded on the screen along with comparable expanding of the grid for further analysis.

75. The apparatus of claims 43, 44 or 45 adapted to display short segments of multiple signals and displaying a long segment of one or a few signals.

76. The apparatus of claims 43, 44 or 45 in which horizontal lines are omitted from the grid.

77. The apparatus of claims 43, 44 or 45 in which the computer is programmed to provide the grid in a gray color.

78. The apparatus of claims 43, 44 or 45 wherein the computer is programmed to display the physiologic signals periodically updated and in which such updating may be halted by an operator.

79. The apparatus of claim 43, 44 or 45 in which vertical lines are omitted from the grid.

80. The apparatus of claims 43, 44 or 45 adapted to display a median waveform of at least one of the physiologic signals.

81. The apparatus of claim 45 in which the computer is programmed so that the vertical and horizontal lines are of two types, major and minor, and wherein the major grid lines are spaced at a larger interval and the minor grid lines are spaced at a smaller interval.

82. The apparatus of claim 81 wherein the computer is programmed to space the major grid lines five times the spacing of the minor grid lines.

83. The apparatus of claim 81 wherein the computer is programmed so that the spacing of the major grid lines is approximately, five millimeters and the spacing of the minor grid lines is approximately one millimeter.

84. The apparatus of claims 43, 44 or 45 wherein the computer is programmed so that the physiologic signal is superposed on the grid to simulate the appearance of a pen drawing on physiologic recording equipment.

85. The apparatus of claim 45 in which the computer is programmed so that the lines of the grid appear to be at least two types differing in thickness.

86. The apparatus of claim 45 in which the computer is programmed so that the lines of the grid appear to be at least two types differing in intensity.

* * * * *

UNITED STATES PATENT AND TRADEMARK OFFICE
CERTIFICATE OF CORRECTION

PATENT NO. : 5,673,702
DATED : October 7, 1997
INVENTOR(S) : Albrecht *et al.*

It is certified that error appears in the above-identified patent and that said Letters Patent is hereby corrected as shown below:

Column 2, Line 28, please delete "Amold" and insert therefor --Arnold--.

Column 3, line 1, please delete "chaff" and insert therefor --chart--.

Column 5, line 41, please delete "falling" and insert therefor --filling--.

Column 6, line 31, please delete "green" and insert therefor --screen--.

Signed and Sealed this

Eleventh Day of May, 1999

Attest:

Q. TODD DICKINSON

*Attesting Officer*       *Acting Commissioner of Patents and Trademarks*